United States Patent [19]

Westenskow et al.

[11] Patent Number: 5,094,235
[45] Date of Patent: Mar. 10, 1992

[54] ANESTHESIA VENTILATING APPARATUS HAVING A BREATHING CIRCUIT AND CONTROL LOOPS FOR ANESTHETIC GAS COMPONENTS

[75] Inventors: Dwayne D. Westenskow, Salt Lake City, Utah; Patrick J. Loughlin, Seattle, Wash.; Roman R. Jaklitsch; Carl-Friedrich Wallroth, both of Lübeck, Fed. Rep. of Germany

[73] Assignee: Drägerwerk Aktiengesellschaft, Lubeck, Fed. Rep. of Germany

[21] Appl. No.: 349,829

[22] Filed: May 10, 1989

[51] Int. Cl.$^5$ .................... A61M 16/00; A62B 7/00; F16K 31/02; G05D 11/02
[52] U.S. Cl. ............. 128/204.22; 128/203.12; 128/205.12; 128/203.25
[58] Field of Search ............ 128/203.12, 204.21, 128/204.22, 203.25, 204.25, 205.12

[56] References Cited

U.S. PATENT DOCUMENTS

| | | | |
|---|---|---|---|
| 3,951,137 | 4/1976 | Conkle et al. | 128/204.22 |
| 4,150,670 | 4/1979 | Jewett et al. | 128/204.22 |
| 4,266,573 | 5/1981 | Braatz | 128/203.25 |
| 4,345,612 | 8/1982 | Koni et al. | 128/203.25 |
| 4,533,346 | 8/1985 | Cosgrove, Jr. et al. | 128/731 |
| 4,550,726 | 11/1985 | McEwen | 128/202.22 |
| 4,631,966 | 12/1986 | Brugnoli | 128/204.22 |
| 4,651,729 | 3/1987 | Rae | 128/204.22 |
| 4,651,730 | 3/1987 | von dem Hagen et al. | 128/204.21 |
| 4,903,693 | 2/1990 | Yasue | 128/203.12 |
| 4,905,685 | 3/1990 | Olsson et al. | 128/204.21 |

FOREIGN PATENT DOCUMENTS

| | | | |
|---|---|---|---|
| 0121255 | 9/1988 | European Pat. Off. | 128/203.12 |
| 0213076 | 8/1984 | Fed. Rep. of Germany | 128/203.25 |

OTHER PUBLICATIONS

"Digital Regelsystem" by Rolf Isermann, pp. 48 to 93, Springer Verlag, New York, 1977.
"Controlled Anaesthesia: A Clinical Evaluation of an Approach Using Patient Characteristics Identified During Uptake", British Journal of Anaesthesia (1983), vol. 55, pp. 1065–1075.

Primary Examiner—Edgar S. Burr
Assistant Examiner—Kimberly L. Asher
Attorney, Agent, or Firm—Walter Ottesen

[57] ABSTRACT

The invention relates to an anesthesia ventilating apparatus having a breathing circuit and a plurality of control loops for the anesthesia gas, the anesthesia agent and the carbon dioxide exhaled by a patient. A disconnect switch is provided for opening and closing the control loop for adjusting the anesthesia agent. When this control loop is opened, a control unit changes the desired value of the anesthetic agent to a desired flushing value thereof. The control unit includes a processor which monitors the time-dependent course of the concentration of the anesthetic agent to determine breathing circuit system parameters and then computes the adjusting parameters of a controller in the control loop for adjusting the anesthetic agent. A method of operating the apparatus is also disclosed.

8 Claims, 3 Drawing Sheets

ANESTHESIA VENTILATING APPARATUS HAVING A BREATHING CIRCUIT AND CONTROL LOOPS FOR ANESTHETIC GAS COMPONENTS

FIELD OF THE INVENTION

The invention relates to an anesthesia ventilating apparatus having a breathing circuit wherein the anesthetic gases necessary for the ventilation can be metered and can be influenced via a control loop. The invention also relates to a method for operating the anesthesia ventilating apparatus.

BACKGROUND OF THE INVENTION

An anesthetic ventilating apparatus having a closed breathing circuit is disclosed in European Patent Publication 0 121 255. This anesthesia ventilating apparatus utilizes a complex control loop for metering anesthetic gas in which the anesthetic gas components are sensed by means of appropriate sensors and the sensor signals are utilized for driving a metering unit. At any time during a ventilation, the fill level of the breathing gas in the breathing circuit is determined and the required fresh gas quantity is supplied.

The control loop for metering the anesthetic gas is essentially conceived for maintaining a quasi-stationary operating condition; that is, the previously adjusted concentration values of the anesthetic gas components are maintained pursuant to a determined unchangeable control algorithm and only as much gas is metered as was consumed.

It is a disadvantage with the known anesthesia ventilating apparatus that for a change of the concentration proportion of individual anesthetic gas components such as the anesthetic agent concentration, new values are reached in part only after substantial adjusting times with the measured concentration in the breathing circuit approximating the new desired value asymptotically. This is for many applications intolerable such as for the transition from the induction phase with higher anesthetic agent concentration to the maintenance phase with lesser concentration.

An anesthesia ventilating apparatus having controlled metering of the anesthesia agent vapor is disclosed in the British Journal of Anaesthesia (1983), 55, pages 1065 to 1075. The breathing system supplying the patient with breathing gas is connected to a ventilator for assisted ventilation and is supplied via a gas metering unit with the anesthetic gases: nitrous oxide, oxygen and anesthetic agents. A central microprocessor controlled control unit on the one hand influences the anesthetic agent metering unit in the manner of a desired-value generator and, on the other hand, registers the actual value which is measured with an anesthetic agent sensor in the breathing system downstream of the patient. When adjusting to a new anesthetic agent desired value, the control unit first supplies an actuating-variable signal to the metering unit which is greater by a multiple than the new desired value which is to be set. This first phase takes approximately nine respiratory cycles and has the purpose of determining parameters specific to the system from the spontaneously adjusting anesthetic agent concentration change in the breathing system. These parameters and further constants stored in the control unit are combined with each other in order to bring the anesthetic agent concentration in the breathing system closer to the new desired value in a stepwise manner during a second phase which has a duration of approximately 90 respiratory cycles. In the third phase, the anesthetic agent concentration is adjusted to the selected desired value by switching in a controller.

It is a disadvantage with this anesthesia ventilating apparatus that a new desired value for the anesthetic agent concentration is adjustable only after a complex measuring and computing program wherein constants from a table have to be considered and inputted to a control unit in advance. The division into three phases is impractical for the clinical routine. Furthermore, there is no direct coupling between the parameters measured in the first phase and the adjusted values of the anesthetic agent controller which is switched in in the third phase.

SUMMARY OF THE INVENTION

It is an object of the invention to provide an anesthesia ventilating apparatus of the kind described above which is so improved that a changed input desired value of an anesthetic gas component is adjustable in a manner which is optimized with respect to time and wherein the controller of the control loop corresponding thereto is automatically adaptable to the system parameters of the breathing circuit. It is also an object of the invention to provide a method for operating the anesthesia ventilating apparatus.

The method of the invention is applied for operating an anesthesia ventilating apparatus having at least one anesthetic gas control loop with a disconnect switch. The apparatus includes a control unit for adjusting a new anesthetic gas desired value S1 performing the following method steps: switching the disconnect switch into the open position during a predetermined time duration; adjusting the anesthetic gas actuating variable at the metering unit in a discontinuous manner to a flushing desired value S2 deviating from the desired value S1; determining the breathing circuit system parameters T1 and T2 from the time-dependent course of the anesthetic gas concentration measured with the measuring unit in at least one of the branches and computing herefrom at least adjusting parameters for the anesthetic gas controller; and, switching the disconnect switch into the closed position when the anesthetic gas concentration value S3 is reached whereby the anesthetic gas controller influences the metering unit to adjust to the desired value S1.

The advantage of the invention is seen essentially in that the control loop is opened for a specific time duration and the breathing circuit can be flushed with the anesthetic gas to be changed. Only when a concentration value in the vicinity of the new desired value to be adjusted is reached, is the control loop again closed, whereby the controller influences the metering unit of the particular anesthetic gas for setting the new desired value. Furthermore, breathing loop system parameters are determined from the time-dependent course of the anesthetic gas concentration and adjusting parameters are computed herefrom for the anesthetic agent controller. The time-dependent course of the anesthetic gas concentration in the breathing circuit is, for example, dependent upon the following: the inflowing gas quantity of the anesthetic gas component; the volume of the breathing circuit and the gas circulation within the breathing circuit. A controller with a fixed adjustment can provide optimal results for only a specific constellation of parameters. A requirement-tailored adaptation of the adjusting parameters is computed from the time-dependent course of the concentration. By means of this adaptation, the controller supplies time-optimized adjusting values specifically also when components of the breathing circuit are changed at intervals, for example, by means of adding tubes between patient and ventilating apparatus. Such modifications can be determined by measuring the time-dependent course of the concentration change.

It is advantageous to use the anesthetic agent concentration as an anesthetic gas component since this must in any event be changed as required by the routine anesthesia method. For example, one works with higher anesthetic agent concentration in the inflowing anesthesia gas during the induction phase and with a lesser concentration of anesthetic agents in the maintenance phase. During the recovery phase at the end of an anesthesia, the anesthesia agent concentration is completely reduced down to the value zero. The oxygen concentration in the breathing circuit is a further anesthetic gas component which can be used. The oxygen concentration is changeable in that the breathing circuit is flushed with oxygen or nitrous oxide. In this connection, the concentration of oxygen cannot however drop below the minimum concentration required for ventilation.

For a concentration change, it is advantageous to adjust the actuating variable to a multiple of the desired value (the flushing desired value S2). For a concentration increase, this factor can go up to a multiple of 10 of the desired value; whereas, with a decrease in concentration, this factor can cause a reduction of the actuating variable to the value zero.

After reaching a multiple of 0.9 of the desired value S1, the control circuit is closed for a concentration increase and the controller influences the actuating variable. The anesthetic gas concentration is now controllable to the previously adjusted desired value. For a concentration reduction, the controller is switched in for a 1.1 multiple of the new desired value S11.

It is advantageous to determine the system parameters of the breathing circuit from the time-dependent course of the particular anesthetic gas concentration. These system parameters result essentially from the washout time of the breathing circuit having the changed anesthetic gas parameter and can be influenced by the following: the anesthetic gas flow, the breathing stroke volume, the breathing frequency and the anesthetic gas uptake by the patient. In addition to the anesthetic agent concentration, it is advantageous to also provide control loops for the oxygen concentration, the breathing circuit volume and the carbon dioxide concentration and to make these control loops connectable via coupling members.

These coupling members are suitable to make dependent variables controllable. For example, if the anesthetic gas flow is increased, the anesthetic agent vapor quantity must likewise be added in order to maintain a constant anesthetic agent concentration in the breathing circuit; that is, the anesthetic agent metering pump must add a higher quantity of fluid to the anesthetic gas flow. In addition, it is advantageous to control the sensitivity of individual controllers in dependence upon specific anesthetic gas parameters. For example, for a closed breathing circuit, the breathing circuit volume controller is the determining component for the metering of anesthetic gas into the breathing circuit since only the volume which has been consumed is added. If in contrast, a quantity of anesthetic gas is metered which is a multiple above that which is consumed as is the case for a half-closed breathing circuit, then the breathing circuit volume controller is of secondary importance since the surplus anesthetic gas is released to the ambient via a surplus gas venting valve after each breath. A sensitivity adaptation is likewise provided for the carbon dioxide controller. The amplification factor is adjusted in dependence upon the breathing circuit volume and the minute volume. For higher breathing minute volumes, that is for a more intense ventilation of the patient, the sensitivity is maximal and the carbon dioxide controller reacts immediately to a change in concentration of carbon dioxide measured in the breathing circuit.

A further coupling member is the adaptation circuit for the anesthetic agent controller which impresses the adjusting parameters on the latter with the desired values being supplied by the control unit.

By coupling the control loops, it is intended that the anesthesia ventilating apparatus automatically selects the most advantageous controller constellation in dependence upon the adjusted ventilating parameters.

It is advantageous to make individual coupling members and individual controllers driveable by the control unit. In this manner, the adjusting parameters of the anesthetic agent controller can for example be computed by the control unit and be transmitted via an adaptation circuit. It is also conceivable that further parameters can be taken into the computation of the controller adjusting parameters such as variables related to the patient such as body weight, body size and the like. This can be required if changes in concentration can be carried out only in a limited manner such as in infants.

It is advantageous to control the sequence of desired value inputs by means of the control unit. For example, if several anesthetic gas components are to be changed simultaneously, priorities for the desired values can be determined by the control unit. An advantageous priority sequence could, for example, be to first adjust the oxygen concentration in the breathing circuit with the supply of oxygen. The anesthetic agent concentration is adjusted for the depth of anesthesia with the second priority stage. The carbon dioxide concentration is controllable by influencing the breathing frequency at the ventilator. The volume control circuit is finally activated when all other control loops are in the steady state in order to adjust the breathing circuit volume to the preselected value.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
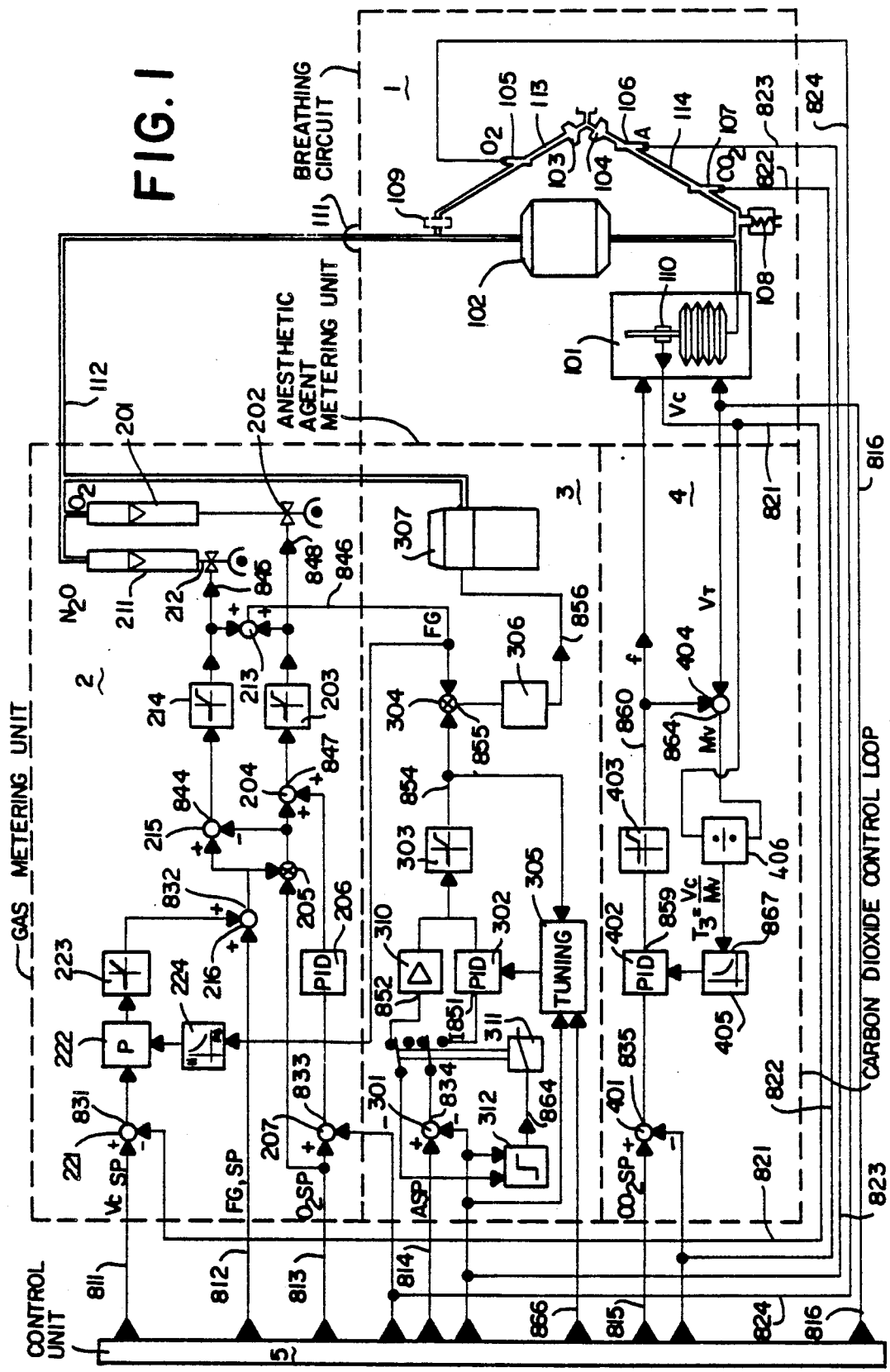
FIG. 1 is a schematic block diagram of the breathing circuit having control loops for the anesthetic gas components.

The anesthesia ventilating apparatus shown in FIG. 1 comprises the breathing circuit 1, the gas metering unit 2 for the anesthetic gas components of oxygen and nitrous oxide, the anesthetic agent metering unit 3, the carbon dioxide control loop 4 and the control unit 5 having an integrated computer portion. The different components are enclosed by a broken line.

The breathing circuit 1 having an uptake branch 113 and an exhale branch 114 takes care of conveying the breathing gas to a patient (not shown). The breathing circuit 1 includes: the ventilator 101 which is preferably configured as a piston-cylinder unit, the carbon dioxide absorber 102 for removing carbon dioxide exhaled by the patient, directional valves (103, 104) for controlling the direction of the breathing gas, sensors (105, 106, 107) for analyzing the components of the anesthetic gas and a surplus gas venting valve 108.

In addition, means are provided for switching a charcoal filter 109 into the breathing circuit 1 as required in order to remove the anesthetic agent delivered by the anesthetic agent metering unit 3 either partially or even completely. This can be necessary when the concentration of the anesthetic agent must be reduced in a short time, for example, during the transition from the induction phase into the maintenance phase of the anesthesia.

The breathing circuit 1 is configured for operation with partial or complete rebreathing whereby a high re-utilization rate of the anesthetic gas is provided. For complete rebreathing, only the gas lost by consumption and leakage must be again delivered.

For analyzing the anesthetic gas components, an oxygen sensor $O_2$ (105) is provided at the inspiratory end and an anesthetic agent sensor A (106) and a carbon dioxide sensor $CO_2$ (107) are provided at the expiratory end.

Anesthetic gas from the gas metering unit 2 and the anesthetic agent metering unit 3 flows via the anesthetic gas connection 111 into the breathing circuit 1. Surplus gas can be removed via the surplus gas venting valve 108.

The gas metering unit 2 meters the anesthetic gases of oxygen and nitrous oxide whose individual throughflow quantities are displayed by means of through-flow measurement tubes (201, 211) and are adjustable via position valves (202, 212) driven by electric motors. The actuating variables for driving the position valves (202, 212) are supplied via the signal connections (848, 845) and are supplied by the oxygen concentration controller 206 and the breathing circuit volume controller 222.

The anesthetic agent metering unit 3 essentially comprises the anesthetic agent metering pump 307, which meters liquid anesthetic agents into the anesthetic gas line 112 where the liquid anesthetic agent vaporizes and mixes with the anesthetic gases (oxygen and nitrous oxide). Alternatively, the anesthetic agent can be injected directly into the breathing circuit 1 with an electrically-driven piston injector. The control of the anesthetic agent metering pump 307 takes place via the signal connection 856 which is connected with the anesthetic agent controller 302 and the amplifier 310.

The carbon dioxide control loop 4 comprises the carbon dioxide controller 402, the carbon dioxide sensor 107 as an actual value sensor and the level detector 110 for the breathing gas quantity in the breathing circuit 1. The actuating variable signal is supplied to the ventilator 101 via the connection 860 in the form of a ventilating frequency. The carbon dioxide concentration in the breathing circuit 1 is adjusted by changing the ventilating frequency.

The control unit 5 having an integrated computer portion is a desired value transmitter for the gas metering unit 2, the anesthetic agent metering unit 3, the carbon dioxide control loop 4 and the breathing stroke volume 816 of the ventilator 101. The signal lines for the following are connected to the control unit 5: breathing circuit volume desired value Vc SP (811), anesthetic gas desired value FG SP (812). oxygen concentration desired value $O_2$ SP (813); anesthetic agent concentration desired value A SP (814); carbon dioxide concentration desired value $CO_2$ SP (815) and breathing stroke volume desired value Vc SP (816).

A closed breathing circuit 1 is first assumed for operation; that is, as much anesthetic gas is delivered as is consumed and lost through leakage.

It is further assumed that an oxygen concentration desired value 813 and a breathing circuit volume desired value 811 are preset at the control unit 5. The anesthetic gas desired value 812 is set to zero for the closed breathing circuit 1 since the anesthetic gas quantity to be delivered is determined alone from the condition applying for the closed system, namely, that the oxygen concentration and the breathing circuit volume are to be held constant in the stationary case. The actual value in the breathing circuit is measured with the oxygen sensor 105 and supplied to the subtraction position 207 via the signal line 824. The output 833 is connected to the oxygen concentration controller 206. The level detector 110 supplies the actual value for the breathing circuit volume Vc and supplies the same to the subtraction position 221 via the signal line 821. The output 831 is connected to the breathing circuit volume controller 222.

The control signal for the anesthetic gas quantity, which must be metered into the breathing circuit 1 per unit of time to maintain the breathing circuit volume at the desired value 811, is formed at the output 832 of the addition position 216.

Specific actuating signals for the anesthetic gas are formed from the control signal at the output 832 and the oxygen concentration desired value 813 via the following: the multiplication position 205, the addition position 204 and the subtraction position 215. The actuating signals specific for the anesthetic gas are supplied to the signal connections (848, 845) of the positioning valves (202, 212) from the outputs 844, 847). The sum of the component gas flows (oxygen $O_2$ and nitrous oxide $N_2O$) measured at the throughflow measuring tubes (211, 201) is proportional to the control signal at the output 832. If this control signal is increased, the gas flows at the throughflow measurement tubes (211, 201) increase by the same amount. If in contrast, the oxygen concentration desired value 813 is changed, for example increased, then this leads to a correspondingly smaller control signal at the output 844 of the subtraction position 215; whereas, the control signal increases at the output of the adding position 204. The nitrous oxide positioning valve 212 is closed in that amount which the oxygen positioning valve 202 is opened. In contrast, the sum of the component gas flows measured at the throughflow measurement tubes (211, 201) remain constant. The limiters (203, 214) limit the signal voltages at the outputs (844, 847) to an upper and lower boundary value which is proportional to the minimal and maximal oxygen gas flow and nitrous oxide gas flow, respectively, which can be delivered.

The breathing gas volume controller 222 is configured as a proportional controller whole amplification is changeable via the characteristic transducer 224 in dependence upon the anesthetic gas flow signal 846. In the closed breathing circuit 1 wherein only the consumed anesthetic gas is substituted, the amplification P of the breathing circuit volume controller 222 is a maximum and the sensitivity of the control loop is thereby likewise a maximum. The breathing loop volume control loop is the determining component for the anesthetic gas metering in the breathing circuit 1. If in contrast thereto, the anesthetic gas desired value 812 is set high as, for example, for a half closed system, then the breathing circuit volume control loop becomes less significant since adequate anesthetic gas is always metered to the breathing circuit 1. The limiter 223 limits the output signal 831 to the upper and lower value for the breathing circuit volume.

The anesthetic agent metering unit 3 adjusts a preselected concentration of he anesthetic agent. The anesthetic agent concentration desired value 814 is compared at the logic component 301 (subtraction position) with the actual value measured by the anesthetic agent sensor 106. The signal line 823 conducting the actual value and the desired value 814 of the anesthetic agent concentration are connected to the limit value switch 312.

The function of the limit value switch 312 will be described in the following.

If the difference signal between the desired value 814 and the actual value transmitted via the signal line 823 exceeds a preset upper limit value, then the limit value switch 312 supplies a control pulse to the disconnect switch 311 via the signal line 364 which then switches into the open position.

The input 852 of the amplifier 310 is connected with the anesthetic agent desired value 814. If the amplification factor of the amplifier 310 is adjusted for example to a factor 10, then the anesthetic agent is metered into the breathing circuit 1 in a quantity increased by a multiple of 10.

If the difference signal at the limit value switch 312 drops beneath a lower preset limit value (that is, the new desired value in the breathing circuit 1 is almost reached), then the disconnect switch 311 switches to its closed position and the input 851 of the anesthetic agent controller 302 is connected with the output 834. The anesthetic agent controller 302 thereby delivers the actuating variable 854 for the anesthesia agent metering unit 307.

The limiter 303 limits the actuating variable 854 to the maximum adjustable concentration, for example to 6% by volume. The control signal 856 for the anesthetic agent metering unit 307 for the quantity of anesthetic agent to be delivered into the breathing circuit 1 is formed from the product 855 of the actuating variable 854 and the anesthetic gas flow FG (846) with this product 855 being formed at the multiplication portion 304. The product 855, charged with the metering rate 306, provides the control signal 856 for the liquid quantity of anesthetic agent which is to be metered into the anesthetic gas line 112 by the anesthetic agent metering unit 3071 The anesthetic agent vapor together with the anesthetic gas is delivered via the anesthetic gas line 112 and the breathing anesthetic gas connection 111 to the circuit 1.

Figure 3:
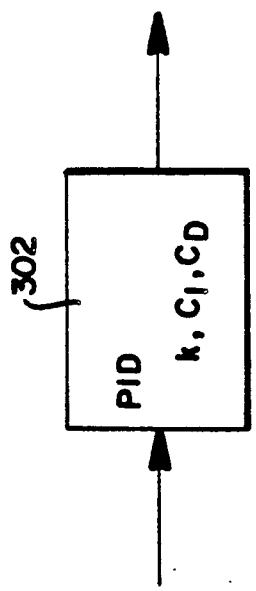

The adjusting parameters of the anesthetic agent controller 302 can be influenced via the adaptation circuit 305. The adaptation circuit 305 is connected via a signal line 866 to the control unit 5 and receives from the latter the desired values for the controller adjusting parameters (FIG. 3). When the controller adjusting parameters are computed, the parameters related to the patient can also be considered which must be previously supplied to the control unit 5.

With the combination of the limit value switch 312 and the disconnect switch 311, it is intended that the anesthetic agent controller 302 be switched out for a certain time when changing the anesthetic agent desired value 814 and that the breathing circuit 1 be flushed with an anesthetic agent concentration deviating from the desired value. Only when the anesthetic agent concentration measured by the anesthetic agent sensor 106 has approximately reached the desired value 814, will the anesthetic agent controller 302 again be switched in in order to control the anesthetic agent concentration to the precise value.

The carbon dioxide control loop 4 adjusts to a specific terminal expiratory carbon dioxide concentration. This parameter can essentially be influenced by the nature of the ventilation, for example, by the ventilating frequency at the ventilator 101. The carbon dioxide desired value $CO_2$ SP (815) and the actual value signal transmitted by the signal line 822 are brought together at the subtraction position 401. The actual value signal is supplied by the carbon dioxide sensor 107. The control deviation at the output 835 is supplied to the carbon dioxide controller 402. The signal at the output 859 is conducted via a limiter 403 which limits the variation range of the actuating variable on connection 860 to values which can be processed by the ventilator 101. The actuating quantity on connection 860 is the ventilating frequency (f) of the ventilator 101, that is, the number of strokes per minute. The amplification factor P of the carbon dioxide controller 402 is adjustable via the characteristic transducer 405. The drive signal 867 for the characteristic transducer 405 is made up of the breathing minute volume signal $M_v$ on signal line (864) formed at the multiplication position 404 and the breathing circuit volume signal $V_c$ (821). The quotient of the breathing circuit volume signal $V_c$ (821) and the breathing minute volume signal $M_v$ (864) yield the drive signal $T_3$ (867) for the characteristic transducer 405. The amplification factor and thereby the sensitivity are a maximum for a larger breathing minute volume signal on signal line 864.

The control signal for the breathing stroke volume $V_s$ (816) is supplied directly to the ventilator 101.

Figure 2:
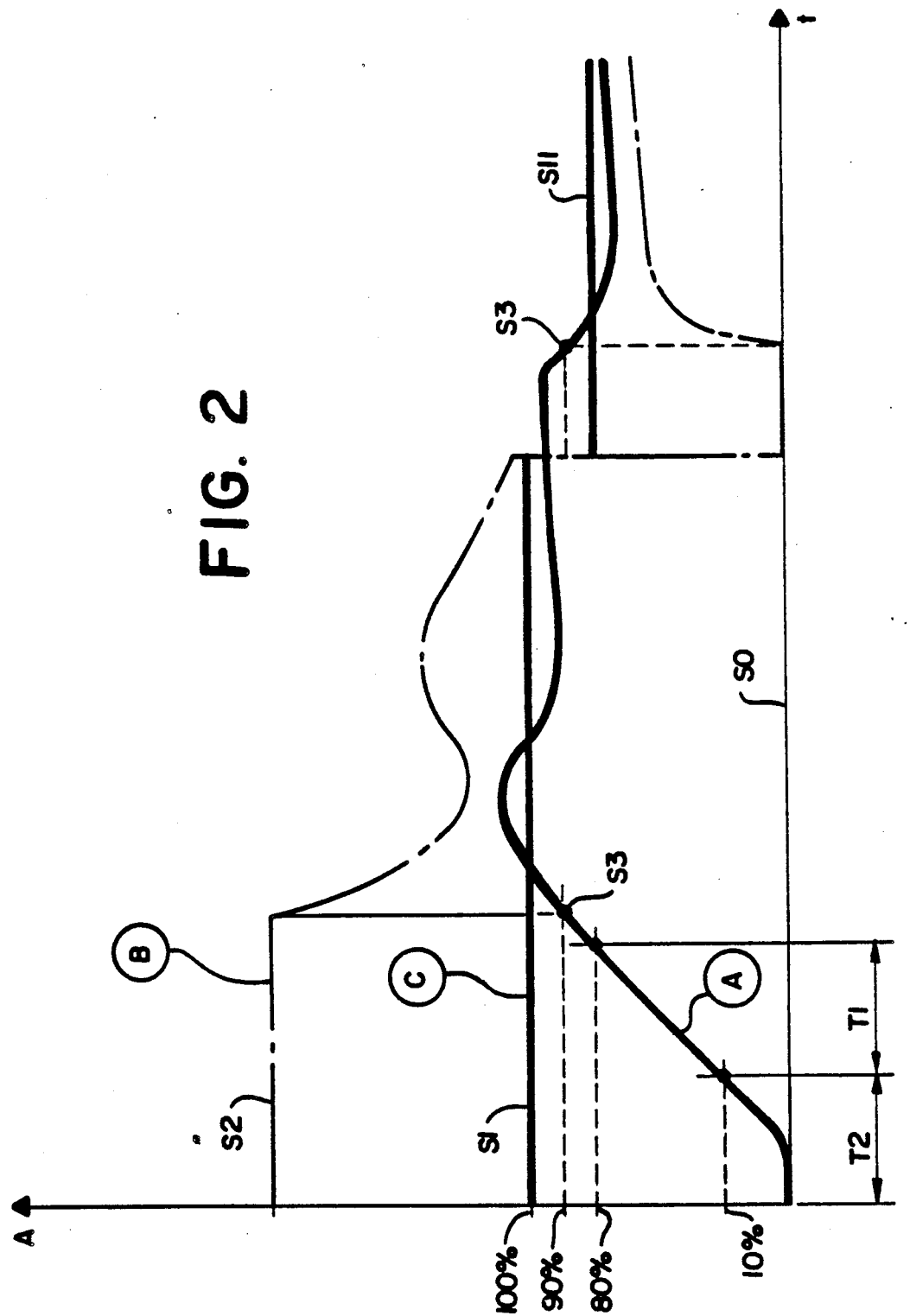
FIG. 2 is a curve showing a jump response when changing the concentration of the anesthetic agent; and, FIG. 3 shows the determination of the controller parameters k, CI, CD obtained from T1 and T2.

An embodiment for the desired value change of the anesthetic agent concentration from S0 to S1 is shown in FIG. 2. The curve A indicates the concentration in the breathing circuit with this concentration being measured by the anesthetic agent sensor 106. Curve B is the anesthetic agent concentration in the anesthetic gas line 112 and curve C are the desired values S1 and S11 which are to be adjusted.

It is assumed that a change of anesthetic agent desired value 814 from S0 to S1 is pregiven at the control unit 5. The limit value switch 312 registers a difference between the actual value measured by the anesthetic agent sensor 106 and the new desired value S1. Since the difference is above the preadjusted limit value, a control pulse is applied to the disconnect switch 311 via the output 364 which causes the disconnect switch to switch over into the open position shown in FIG. 1. The anesthetic agent desired value 814 is connected to the input 852 of the amplifier 310. By means of the amplifier, a dosage increased by the amplification factor and in a form of a flushing desired value S2 is adjusted at the anesthetic agent metering pump 307. If the new desired value S1 is, for example, 0.5% by volume and the amplification factor is 10, then anesthetic agent in the amount of 5% by volume is metered into the breathing circuit 1 as a flushing desired value S2.

The system parameters T2 and T1 (curve A) are determined from the discontinuous response of the anesthetic agent concentration measured by the anesthetic agent sensor 106. For a desired value change of S0 to S1, the time point is set to zero by a timing signal generator in the control unit 5. The concentration change measured by the anesthetic agent sensor 106 is continuously registered by the control unit 5 beginning from the start point. The system parameter T2 is then the time until the 0.1 portion of the desired value S1 is reached and the sum of T1 and T2 is the time until the 0.8 portion of the desired value S1 is reached. The system parameters T1 and T2 describe the instantaneous condition of the breathing circuit 1 and are dependent, for example, on the anesthetic gas flow metered by the gas metering unit 2 into the breathing circuit 1 and the ventilating parameters adjusted at the ventilator 101 such as the breathing frequency (f) and the breathing stroke volume $V_s$.

If the anesthetic agent concentration has reached the 0.9 portion of desired value S1, and thereby the point S3, then the disconnect switch 311 switches in the closure direction and the anesthetic agent controller 302 influences the anesthetic agent metering pump 307 for adjusting the new desired value in the breathing circuit 1.

From the measured system parameters T1 and T2, adjusting parameters for the anesthetic agent controller 302 are computed in the adaptation circuit 305 and impressed on the controller 302. For this purpose, it is advantageous to carry out portions of the computation in the control unit 5 and to transmit the signals via a control line 866 to the adaptation circuit 305. In addition, parameters of the patient can be inputted into the control unit 5 and considered when computing The mathematical interrelationship between the system parameters T1 and T2 and the adjusting parameters (k, $C_I$, $C_D$) of the anesthetic agent controller 302 are given in FIG. 3. These computation formulas are based on the optimizing criteria of Ziegler and Nichols as described in the technical paper entitled "Optimum Setting for Automatic Controllers", Transaction of the A.S.M.E., November 1942.

The anesthetic ventilating apparatus of the invention is for administering anesthesia to a patient. The apparatus of the invention can, for example, include the following: a breathing circuit 1 for supplying respiratory gas containing an anesthetic agent to the patient and having first and second branches (113 and 114); a carbon dioxide absorber 102 disposed in one of said branches for removing carbon dioxide exhaled by the patient; a first control loop for generating a first actuating variable in response to which the amount of respiratory gas supplied to said breathing circuit 1 is adjusted; said first control loop including: an anesthetic gas metering unit 2 for receiving said first actuating variable and metering the respiratory gas into the breathing circuit 1 in response to said first actuating variable; and, an anesthetic gas controller 206 connected to said metering unit for operating on said first actuating variable and having a set of adjusting parameters; a second control loop for generating a second actuating variable in response to which the amount of anesthetic agent supplied to said breathing circuit 1 is adjusted; said second control loop including: an anesthetic agent metering unit 3 for receiving said second actuating variable and metering the anesthetic agent into the breathing circuit 1 in response to said second actuating variable; and, an anesthetic agent controller 302 connected to said metering unit for operating on said second actuating variable and having a set of adjusting parameters; a third control loop for generating a third actuating variable in response to which a ventilating frequency in said breathing circuit is adjusted; said third control loop including: a ventilating unit 101 for receiving said third actuating variable and adjusting said ventilating frequency in said breathing circuit in response to said third actuating variable; and, a carbon dioxide controller 402 connected to said ventilating unit 101 and having a set of adjusting parameters; coupling means (205, 224, 304, 305 and/or 405) for coupling two of said loops so as to permit one of said actuating values to change another one of said actuating values; a control unit 5 for supplying: an anesthetic gas desired value to said first control loop; an anesthetic agent desired value to said second control loop; and, a carbon dioxide desired value to said third control loop; said control unit 5 including means for changing one of said desired values from a desired first value to a desired second value in a discontinuous jump-like manner; an oxygen sensor 105 of said first control loop for measuring the anesthetic gas actual value present in said breathing circuit 1; an anesthetic agent sensor 106 of said second control loop for measuring the anesthetic agent actual value present in said breathing circuit 1; a carbon dioxide sensor 107 of said third control loop for measuring the carbon dioxide actual value present in said breathing circuit; a logic component (207, 301 or 401) for receiving one of said desired values for one of said control loops and one of said actual values corresponding to said one control loop for forming a closed loop control signal; switch means 311 switchable between an open position wherein said one control loop is opened and connected to said control unit 5 for receiving and applying said desired second value to said unit of said one control loop and a closed position wherein said one control loop is closed and connected to said logic component for receiving and applying said closed loop control signal to the controller of said one control loop; limit means 312 responding to said change from said desired first value to said desired second value for switching said switch means 311 from said closed position to said open position for a predetermined time duration; said control unit 5 including processing means monitoring the sensor corresponding to said one control loop for determining breathing circuit system parameters T1 and T2 and computing said adjusting parameters of the controller of said one control loop; and, said limit means 312 being connected to the one sensor of said one control loop and responding to a predetermined value measured by said one sensor for switching said switch means back into said closed position so as to permit said controller of said one control loop to adjust the actuating variable of said one control loop so as to cause said unit of said one control loop to readjust the concentration of the substance measured by said one sensor to said first desired value.

It is understood that the foregoing description is that of the preferred embodiments of the invention and that various changes and modifications may be made thereto without departing from the spirit and scope of the invention as defined in the appended claims.

What is claimed is:

1. Anesthetic ventilating apparatus for administering anesthesia to a patient, the apparatus comprising:
   a closed-loop breathing circuit for supplying and recirculating respiratory gas containing an anesthetic agent to the patient and having first and second branches;
   a carbon dioxide absorber disposed in one of said branches for removing carbon dioxide exhaled by the patient;
   a gas metering unit supplying anesthetic gases into said breathing circuit;
   said gas metering unit including: an oxygen sensor for measuring the oxygen content in said breathing circuit; and, an oxygen concentration controller connected to said oxygen sensor for determining the quantity of oxygen to be metered into the breathing circuit and for generating a first actuating variable in response to which oxygen is supplied to said breathing circuit;
   said gas metering unit further including: a level detector for measuring the breathing circuit volume; and, a breathing circuit volume controller connected to said level detector for generating a second actuating variable in response to which anesthetic gas is supplied to said breathing circuit;
   an anesthetic agent metering unit for generating a third actuating variable in response to which the amount of an anesthetic agent supplied to said breathing circuit is adjusted;
   an anesthetic agent controller connected to said anesthetic agent metering unit and having a set of adjusting parameters;
   coupling means for coupling two of said controllers so as to permit one of said actuating values to change another one of said actuating values;
   a control unit for changing the concentration of the anesthetic agent supplied by said anesthetic agent metering unit from a first desired value S1 to a second desired value S2 in a discontinuous jump-like manner with said second desired value S2 being a flushing concentration by volume of said anesthetic agent which is many times greater than the concentration by volume of said anesthetic agent corresponding to said first desired value S1;
   said anesthetic agent metering unit with said anesthetic agent controller and said control unit conjointly defining a normally closed control loop;
   an anesthetic agent sensor for measuring the anesthetic agent actual value present in said breathing circuit;
   a logic component for receiving said first desired value S1 of said anesthetic agent and said anesthetic agent actual value for forming a closed loop control signal;
   said control unit including:
   (a) limit means for registering a difference between said actual value and said first desired value S1 of anesthetic agent in said breathing circuit and for emitting an output signal for a predetermined duration when said difference exceeds a predetermined limit;
   (b) a disconnect switch having an output and being switchable in response to said output signal from a first position wherein said normally closed control loop is closed and wherein said logic component is connected to said anesthetic agent controller for applying said closed loop control signal thereto to a second position wherein said normally closed control loop is opened and wherein said first desired value S1 is applied to said output; and,
   (c) amplifier means connected to said output of said disconnect switch for receiving said desired value S1 when said disconnect switch is in said second position and having an amplification for amplifying said first desired value S1 many times to form said second desired value S2 indicative of said flushing concentration of said anesthetic agent;
   said control unit further including processing means monitoring the concentration of the anesthetic agent measured by said anesthetic agent sensor for determining first and second breathing circuit system parameters (T1 and T2) and for computing said adjusting parameters for said anesthetic agent controller;
   said first breathing circuit parameter T1 representing the time to reach a first percentage value of the desired anesthetic concentration and said second breathing circuit parameter T2 representing the time required to reach a second percentage value of the desired anesthetic concentration starting from an initial value SO of anesthetic medium in said breathing circuit;
   said limit means being connected to said anesthetic agent sensor and responding to a predetermined value S3 of the concentration of said anesthetic agent in said breathing circuit for switching said disconnect switch back into said first position so as to permit said anesthetic agent controller to adjust said second actuating variable so as to cause said anesthetic agent metering unit to readjust the concentration of said anesthetic agent to said first desired value S1;
   the concentration of said anesthetic agent S3 corresponding to approximately (0.9) (S1) when the concentration of the agent is increased and corresponding to approximately (1.1) (S11) when the concentration of the agent is reduced, said S11 being a new desired value applied to said normally closed control loop by said control unit when said disconnect switch is again in said first position;
   said system parameter T2 corresponding to the time required to achieve said concentration of approximately (0.1) (S1) when increasing the concentration of the agent in said breathing circuit; and,
   the sum of said system parameters (T1+T2) corresponding to the time required to achieve approximately (0.8) (S1) when increasing the concentration of the agent in said breathing circuit.

2. The anesthetic ventilating apparatus of claim 1, said amplification being selected for amplifying said value S2 up to ten times when increasing the concentration of said anesthetic agent in said breathing circuit thereby permitting said value S2 to be adjusted up to ten times of said value S1 and for reducing said value S2 to zero when reducing the concentration of said anesthetic agent in said breathing circuit.

3. The anesthetic ventilating apparatus of claim 1, wherein said coupling means is a transducer connected between two of said controllers.

4. The anesthetic ventilating apparatus of claim 1, wherein said control unit supplies desired values to respective ones of said controllers corresponding to said actuating variables; and, said control unit including sequence control means for fixing the sequence with which said desired values are applied.

5. The anesthetic ventilating apparatus of claim 4, further comprising a carbon dioxide control loop for adjusting the ventilating rate in said breathing circuit; and, wherein the respiratory gas includes oxygen as a component and wherein said gas metering unit includes oxygen supply means for adjusting the supply of oxygen contained in said respiratory gas; and, wherein said sequence control means is adapted to first operate on said oxygen supply means of said gas metering unit to first adjust the oxygen concentration in said breathing circuit; to thereafter operate on said anesthetic metering unit to adjust the concentration of anesthetic agent in said breathing circuit to thereby adjust the depth of the anesthesia; and to then operate on said carbon dioxide control loop to adjust the ventilating rate in said breathing circuit.

6. Anesthetic ventilating apparatus for administering anesthesia to a patient, the apparatus comprising:
   a closed-loop breathing circuit for supplying respiratory gas containing an anesthetic agent to the patient and having first and second branches;
   a carbon dioxide absorber disposed in one of said branches for removing carbon dioxide exhaled by the patient;
   a first closed control loop for generating a first actuating variable in response to which the amount of respiratory gas supplied to said breathing circuit is adjusted;
   said first closed control loop including: an anesthetic gas metering unit for receiving said first actuating variable and metering the respiratory gas into the breathing circuit in response to said first actuating variable; and, an anesthetic gas controller connected to said metering unit for operating on said first actuating variable and having a set of adjusting parameters; a second closed control loop for generating a second actuating variable in response to which the amount of anesthetic agent supplied to said breathing circuit is adjusted;
   said second closed control loop including: an anesthetic agent metering unit for receiving said second actuating variable and metering the anesthetic agent into the breathing circuit in response to said second actuating variable; and, an anesthetic agent controller connected to said metering unit for operating on said second actuating variable and having a set of adjusting parameters;
   a third closed control loop for generating a third actuating variable in response to which a ventilating frequency in said breathing circuit is adjusted;
   said third closed control loop including: a ventilating unit for receiving said third actuating variable and adjusting said ventilating frequency in said breathing circuit in response to said third actuating variable; and, a carbon dioxide controller connected to said ventilating unit and having a set of adjusting parameters;
   coupling means for coupling two of said loops so as to permit one of said actuating values to change another one of said actuating values;
   a control unit for changing the concentration of the anesthetic agent supplied by said anesthetic agent metering unit from a first desired value S1 to a second desired value S2 in a discontinuous jump-like manner with said second desired value S2 being a flushing concentration by volume of said anesthetic agent which is many times greater than the concentration by volume of said anesthetic agent corresponding to said first desired value S1;
   said anesthetic agent metering unit with said anesthetic agent controller and said control unit conjointly defining said second closed control loop as a normally closed control loop;
   an oxygen sensor of said first control loop for measuring the anesthetic gas actual value present in said breathing circuit;
   an anesthetic agent sensor of said second control loop for measuring the anesthetic agent actual value present in said breathing circuit;
   a carbon dioxide sensor of said third control loop for measuring the carbon dioxide actual value present in said breathing circuit;
   a logic component for receiving said first desired value S1 of said anesthetic agent and said anesthetic agent actual value for forming a closed loop control signal;
   said control unit including:
   (a) limit means for registering a difference between said actual value and said first desired value S1 of anesthetic agent in said breathing circuit and for emitting an output signal for a predetermined duration when said difference exceeds a predetermined limit;
   (b) a disconnect switch having an output and being switchable in response to said output signal from a first position wherein said normally closed control loop is closed and wherein said logic component is connected to said anesthetic agent controller for applying said closed loop control signal thereto to a second position wherein said normally closed control loop is opened and wherein said first desired value S1 is applied to said output; and,
   (c) amplifier means connected to said output of said disconnect switch for receiving said desired value S1 when said disconnect switch is in said second position and having an amplification for amplifying said first desired value S1 many times to form said second desired value S2 indicative of said flushing concentration of said anesthetic agent;
   said control unit further including processing means monitoring the concentration of the anesthetic agent measured by said anesthetic agent sensor for determining breathing circuit system parameters T1 and T2 and computing said adjusting parameters of said anesthetic agent controller of said second closed control loop;
   said first breathing circuit parameter T1 representing the time to reach a first percentage value of the desired anesthetic concentration and said second breathing circuit parameter T2 representing the time required to reach a second percentage value of the desired anesthetic concentration starting from an initial value SO of anesthetic medium in said breathing circuit;
   said limit means being connected to said anesthetic agent sensor and responding to a predetermined value S3 of the concentration of said anesthetic agent in said breathing circuit for switching said disconnect switch back into said first position so as to permit said anesthetic agent controller to adjust said second actuating variable so as to cause said anesthetic agent metering unit to readjust the concentration of said anesthetic agent to said first desired value S1;

the concentration of said anesthetic agent S3 corresponding to approximately (0.9) (S1) when the concentration of the agent is increased and corresponding to approximately (1.1) (S11) when the concentration of the agent is reduced, said S11 being a new desired value applied to said normally closed control loop by said control unit when said disconnect switch is again in said first position;

said system parameter T2 corresponding to the time required to achieve said concentration of approximately (0.1) (S1) when increasing the concentration of the agent in said breathing circuit; and, the sum of said system parameters (T1+T2) corresponding to the time required to achieve approximately (0.8) (S1) when increasing the concentration of the agent in said breathing circuit.

7. The anesthetic ventilating apparatus of claim 6, said coupling means being a transducer coupling two of said loops.

8. The anesthetic ventilating apparatus of claim 7, said transducer being a first transducer coupling said first and second control loops and said apparatus further including a second transducer for coupling said second and third loops.

* * * * *

UNITED STATES PATENT AND TRADEMARK OFFICE
CERTIFICATE OF CORRECTION

PATENT NO. : 5,094,235

DATED : March 10, 1992

INVENTOR(S) : Dwayne D. Westenskow, Patrick J. Loughlin, Roman R. Jaklitsch and Carl-Friedrich Wallroth It is certified that error appears in the above-identified patent and that said Letters Patent is hereby corrected as shown below:

In column 4, line 60: delete "CI, CD" and substitute -- $C_I$, $C_D$ -- therefor.

In column 6, line 5: delete "." and substitute -- , -- therefor.

In column 6, line 43: before "848, 847)", insert -- ( --.

In column 7, line 53: delete "portion" and substitute -- position -- therefor.

In column 7, line 58: delete "3071" and substitute -- 307. -- therefor.

In column 7, line 60: delete "breathing".

In column 7, line 61: before "circuit 1", insert -- breathing --.

UNITED STATES PATENT AND TRADEMARK OFFICE
CERTIFICATE OF CORRECTION

PATENT NO. : 5,094,235

DATED : March 10, 1992

INVENTOR(S) : Dwayne D. Westenskow, Patrick J. Loughlin, Roman R. Jaklitsch and Carl-Friedrich Wallroth It is certified that error appears in the above-identified patent and that said Letters Patent is hereby corrected as shown below:

In column 9, line 38: after "computing", insert -- the adjusting parameters. --.

In column 13, line 38: after "parameters;", start a new paragraph.

Signed and Sealed this

Twenty-second Day of June, 1993

Attest:

MICHAEL K. KIRK

Attesting Officer

Acting Commissioner of Patents and Trademarks